(12) United States Patent
Colonna et al.

(10) Patent No.: US 11,952,417 B2
(45) Date of Patent: Apr. 9, 2024

(54) ANTI-IL12RB1 ANTIBODIES

(71) Applicant: Washington University, St. Louis, MO (US)

(72) Inventors: Marco Colonna, St. Louis, MO (US); Cristiane Secca da Silva, St. Louis, MO (US)

(73) Assignee: Washington University, St. Louis, MO (US)

( * ) Notice: Subject to any disclaimer, the term of this patent is extended or adjusted under 35 U.S.C. 154(b) by 84 days.

(21) Appl. No.: 17/546,801

(22) Filed: Dec. 9, 2021

(65) Prior Publication Data

US 2022/0177567 A1    Jun. 9, 2022

Related U.S. Application Data

(60) Provisional application No. 63/123,075, filed on Dec. 9, 2020.

(51) Int. Cl.
*A61K 39/395*    (2006.01)
*A61P 37/02*     (2006.01)
*C07K 16/24*     (2006.01)
*A61K 39/00*     (2006.01)

(52) U.S. Cl.
CPC .......... *C07K 16/244* (2013.01); *A61P 37/02* (2018.01); *C07K 16/241* (2013.01); *A61K 2039/507* (2013.01); *C07K 2317/33* (2013.01); *C07K 2317/34* (2013.01); *C07K 2317/56* (2013.01); *C07K 2317/76* (2013.01)

(58) Field of Classification Search
None
See application file for complete search history.

(56) References Cited

PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

\* cited by examiner

*Primary Examiner* — Christine J Saoud
*Assistant Examiner* — Jon M Lockard
(74) *Attorney, Agent, or Firm* — Polsinelli PC

(57) ABSTRACT

The present invention is directed towards isolated antibodies that bind to IL12Rβ1. Specifically, anti-IL12Rβ1 antibodies, and methods of treatment using the antibodies are disclosed. The antibody is targeted against the beta 1 subunit of the receptors of IL-12 and IL-23 and is capable of blocking signaling by inflammatory cytokines IL-12 and IL-23, which could be useful in treating autoimmune inflammatory diseases, such as inflammatory bowel disease (IBD), RA, and psoriasis.

18 Claims, 9 Drawing Sheets
(9 of 9 Drawing Sheet(s) Filed in Color)
Specification includes a Sequence Listing.

```
-----CDR1--->   <---CDR2--->   <----CDR3----
GYTFTSYW....    IDPNNGYT..     VRGGEIYYFDY
QDIYKY......    YTS......      LQYDNILWT
```

Signal Peptide (blue), Variable (yellow) and Constant Region Sequences

A1439-1G6-D10
VH (Variable Heavy)

CDR Analysis
A1439HC.6795    GYTFTSYW....    IDPNNGYT..    VRGGEIYYFDY

Amino Acid Sequence in FASTA Format
> A1439HC.6795
MERHWIFLSLLSVIAGVHSRVQLQQSGAELAKPGASVRLSCMASGYTFTSYWMHWVKQRP
GQGLEWIGYIDPNNGYTKYSQKFKDKATLTADKSSSTANMRLSSLTYEDSAVYYCVRGGE
IYYFDYWGQGTTLTVSSAKTTPPSVYPLAPGCGDTTGSSVTLGCLVKGYFPESVTVTWNS
GSLSSSVHTFPALLQSGLYTMSSSVTVPSS

Nucleotide Sequence in FASTA Format
> A1439HC.6795
ATGGAAAGGCACTGGATCTTTCTCTCCCTGTTGTCAGTAATAGCAGGTGTCCACTCCCGGGTCCAG
CTGCAGCAGTCCGGGGCTGAACTGGCAAAACCTGGGGCCTCCGTGAGGCTGTCCTGCATGGCTT
CTGGCTACACCTTTACCAGCTACTGGATGCACTGGGTAAAACAGAGGCCTGGACAGGGTCTGGAA
TGGATTGGATACATTGATCCTAACAATGGTTATACTAAGTACAGTCAGAAGTTCAAGGACAAGGCCA
CATTGACTGCAGACAAATCCTCCAGCACAGCCAATATGCGGCTGAGCAGCCTGACATATGAGGACT
CTGCAGTCTATTACTGTGTAAGGGGGGGAGAGATTTACTACTTTGACTACTGGGGCCAAGGCACCA
CTCTCACAGTCTCCTCAGCCAAAACAACACCCCCATCAGTCTATCCACTGGCCCCTGGGTGTGGAG
ATACAACTGGTTCCTCTGTGACTCTGGGATGCCTGGTCAAGGGCTACTTCCCTGAGTCAGTGACTG
TGACTTGGAACTCTGGATCCCTGTCCAGCAGTGTGCACACCTTCCCAGCTCTCCTGCAGTCTGGAC
TCTACACTATGAGCAGCTCAGTGACTGTCCCCTCCAGC

Signal Peptide (blue), Variable (yellow) and Constant Region Sequences

VL (Variable Light)

CDR Analysis
A1439LC.6842    QDIYKY......    YTS.......    LQYDNILWT

Amino Acid Sequence in FASTA format
> A1439LC.6842
MRPSIQFLGLLLFWLHGGQCDIQMTQSPSSLSASLGGKVTITCKASQDIYKYIAWYQHKPGKG
PRLLIHYTSTLQPGIPSRFSGSGSGRDYSFSISDLEPEDIATYYCLQYDNILWTFGGGTKLEIKR
ADAAPTVSIFPPSSEQLTSGGASVVCFLNNFYPKDINVKWKIDGSERQNGVLNSWTDQDSKD
STYSMSSTLTLTK

Nucleotide Sequence in FASTA format
> A1439LC.6842
ATGAGACCGTCTATTCAGTTCCTGGGGCTCTTGTTGTTCTGGCTTCACGGTGGTCAGTGTGACATC
CAGATGACACAGTCTCCATCCTCACTGTCTGCATCGCTGGGAGGCAAAGTCACCATCACTTGCAAG
GCAAGCCAAGACATTTACAAGTATATTGCTTGGTACCAACACAAGCCTGGAAAAGGTCCTAGGCTG
CTCATACATTACACATCTACATTGCAGCCAGGCATCCCATCAAGGTTCAGTGGAAGTGGGTCTGGG
AGAGATTATTCCTTCAGCATCAGCGACCTGGAGCCTGAAGATATTGCAACTTATTATTGTCTACAGT
ATGATAATATTCTGTGGACGTTCGGTGGAGGCACCAAGCTGGAAATCAAACGGGCTGATGCTGCA
CCAACTGTATCCATCTTCCCACCATCCAGTGAGCAGTTAACATCTGGAGGTGCCTCAGTCGTGTGC
TTCTTGAACAACTTCTACCCCAAAGACATCAATGTCAAGTGGAAGATTGATGGCAGTGAACGACAAA
ATGGCGTCCTGAACAGTTGGACTGATCAGGACAGCAAAGACAGCACCTACAGCATGAGCAGCACC
CTCACGTTGACCAAG
```

FIG. 9

ANTI-IL12RB1 ANTIBODIES

FIELD OF THE DISCLOSURE

The invention relates to anti-IL12Rβ1 antibodies, compositions comprising anti-IL12Rβ1 antibodies and to uses thereof. The disclosure also relates to methods for the prevention, treatment, and/or management of inflammatory and/or autoimmune diseases.

REFERENCE TO SEQUENCE LISTING

This application contains a Sequence Listing that has been submitted in ASCII format via EFS-Web and is hereby incorporated by reference in its entirety. The ASCII copy, created on Dec. 8, 2021, is named Untitled_ST25.txt, and is 6,829 bytes in size.

BACKGROUND

Interleukin-12 (IL-12) is a heterodimeric cytokine consisting of glycosylated polypeptide chains of 35 and 40 kD which are disulfide bonded. IL-12 mediates a variety of biological processes and has been referred to as NK cell stimulatory factor (NKSF), T-cell stimulating factor, cytotoxic T-lymphocyte maturation factor and EBV-transformed B-cell line factor. IL-12 is produced by innate cells, including macrophages and dendritic cells, and drives the differentiation of naïve T cells into T helper type 1 cells producing IFN-γ. Although the function of IL-12 in driving Th1 responses is a protective feature in several intracellular microbial infection models, IL-12 gained notoriety as the cytokine promoting a wide variety of inflammatory responses associated with autoimmune diseases. In mice and humans, IL-12 is composed of the IL-12p40 subunit linked to the IL-12p35 subunit, and signals through the IL-12 receptor made up of IL-12Rβ1 and IL-12Rβ2 subunits. Experimental studies demonstrated mice lacking IL-12p40 or the IL-12β1 receptor were more resistant in autoimmune models, including collagen-induced arthritis and experimental autoimmune encephalomyelitis. Studies using neutralizing antibodies to IL-12p40 in mouse models of inflammation further established that targeting IL-12 may be an attractive therapy for reducing the pathological conditions associated with autoimmune diseases and inflammation.

IL-23 a cytokine produced by dendritic cells and macrophages, is composed of IL-12p40, which pairs with an IL-23p19 subunit and signals through the IL-23R and the shared subunit IL-12Rβ1. The ability of IL-12 to induce the differentiation of naïve T cells into IFN-γ-producing Th1 cells, and that of IL-23 to drive the expansion of IL-17-producing T cell population, are suggestive of IL-12 and IL-23 involvement in autoimmunity and chronic inflammation. Animal model studies identified that mice deficient in the expression of the p40 subunit of IL-12/23 were protected from developing arthritis and ocular or bowel inflammatory conditions after immunization with specific antigens. However, it is very likely that IL-12 and IL-23 also have divergent immune functions, as it was subsequently found that mice lacking IL-12 (p35) were highly susceptible to experimental autoimmune encephalomyelitis (EAE), whereas IL-12/23 p40-deficient mice were completely resistant to developing this pathology. Further studies, showing the equivalence of the phenotypes of the two mice (lacking the IL-23 p19 or IL-12/23 p40 subunits), suggested that IL-23, rather than IL-12, is the major orchestrator of autoimmunity. In addition to animal models, the presence of these two cytokines at the site of autoimmune inflammation in various human pathologies has provided additional rationale for their use as therapeutic targets. For example, resistance to anti-TNFα therapy is associated with an increased expression of IL-23 and IL-23R in the mucosa of Crohn's disease patients during treatment.

Accordingly, there is a need to provide anti-IL12Rβ1 antibodies capable of blocking signaling by inflammatory cytokines IL-12 and IL-23, and are useful in treating autoimmune and/or inflammatory diseases, such as inflammatory bowel disease (IBD), ulcerative colitis, Crohn's disease, rheumatoid arthritis, and psoriasis.

Other aspects and iterations of the invention are detailed below.

BRIEF DESCRIPTION OF THE FIGURES

The application file contains at least one photograph executed in color. Copies of this patent application publication with color photographs will be provided by the Office upon request and payment of the necessary fee.

FIG. 9 shows the CDRs, Variable Heavy (VH), and Variable Light (VL) sequences corresponding to an exemplary antibody of the disclosure (1G6. VH CDR1 comprises the sequence GYTFTSYW (SEQ ID NO: 1), VH CDR2 comprises the sequence IDPNNGYT (SEQ ID NO: 2), VH CDR3 comprises the sequence VRGGEIYYFDY (SEQ ID NO: 3); Variable Light (VL) CDR1 comprises the sequence QDIYKY (SEQ ID NO: 4), VL CDR2 comprises the sequence YTS, and VL CDR3 comprises the sequence LQYDNILWT (SEQ ID NO: 5). The 1G6 VH comprises the amino acid sequence named A1439HC.6795 (SEQ ID NO: 6). An 1G6 VH coding nucleic sequence is shown for A1439HC.6795 (SEQ ID NO: 8). The 1G6 VL comprises the amino acid sequence named A1439LC.6842 (SEQ ID NO: 7). The 1G6 VL coding nucleic sequence is shown for A1439LC.6842 (SEQ ID NO: 9).

DETAILED DESCRIPTION

Figure 1:
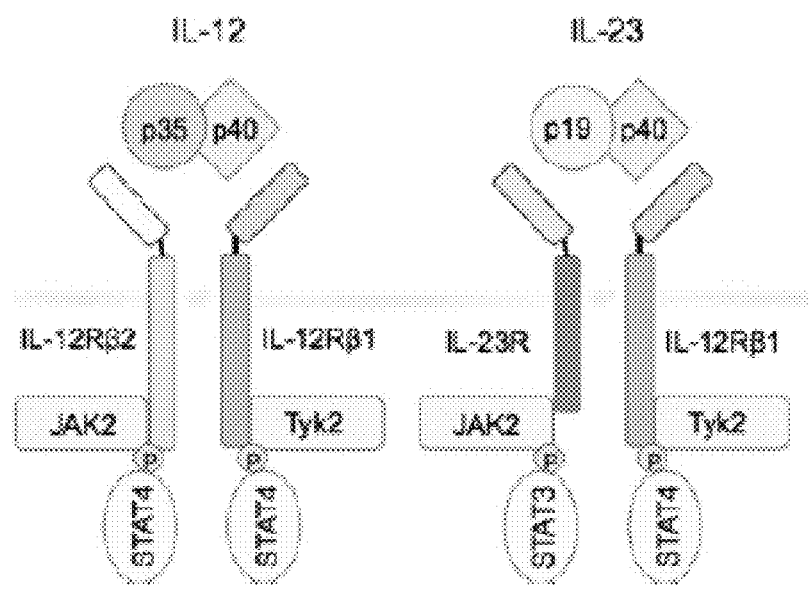
FIG. 1 is a cartoon showing IL-12 and IL-23 signaling including through the shared IL-12Rβ1 subunit.

Applicants have discovered anti-IL12Rβ1 antibodies and methods of using the anti-IL12Rβ1 antibodies to block signaling by inflammatory cytokines IL-12 and IL-23. The anti-IL12Rβ1 antibodies can be used to treat, prevent, and or manage autoimmune and/or inflammatory diseases, such as inflammatory bowel disease (IBD), rheumatoid arthritis, and psoriasis. In various aspects, an anti-IL12Rβ1 antibody of the disclosure binds with high affinity to IL12Rβ1, a common chain shared between IL-12R and IL-23R. IL12Rβ1 is essential for both IL-12 and IL-23 signaling and an anti-IL12Rβ1 antibody of the disclosure abrogates IL-23 and/or IL-12 activation of human innate lymphocytes. It is believed that no high affinity antagonist antibodies are known to block the receptors for IL-12 and IL-23, which is possibly due to the complexity of the receptor structure which makes the generation of such antibodies much more difficult than the generation of antibodies specific for the cytokines themselves (e.g., mAbs against IL-12, IL-23, or subunits thereof). In some embodiments, an anti-IL12Rβ1 antibody of the disclosure may be an alternative therapeutic to Ustekinumab or used in combination with Ustekinumab and provide more advantageous properties due to the observation that the pathogenic T helper cells express high levels of IL12Rβ1 suggesting these cells might be preferentially targeted by an antibody of the disclosure.

I. Definitions

The term "a" or "an" entity refers to one or more of that entity; for example, a "polypeptide subunit" is understood to represent one or more polypeptide subunits. As such, the terms "a" (or "an"), "one or more," and "at least one" can be used interchangeably herein.

Furthermore, "and/or" where used herein is to be taken as specific disclosure of each of the specified features or components with or without the other. Thus, the term "and/or" as used in a phrase such as "A and/or B" herein is intended to include "A and B," "A or B," "A" (alone), and "B" (alone).

Unless defined otherwise, technical and scientific terms used herein have the same meaning as commonly understood by one of ordinary skill in the art to which this disclosure is related.

Where applicable, units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. Nucleic acid sequences are written from 5' to 3', left to right.

The headings provided herein are not limitations of the various aspects and embodiments of the disclosure, which can be had by reference to the specification as a whole.

Terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of amino acid monomers linearly linked by peptide bonds (also known as amide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, hydrophobic interactions, etc., to produce, e.g., a multimeric protein.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, insertions, and/or deletions. Derivatives are polypeptides that have been altered so as to exhibit additional features not found on the native polypeptide, such as increased resistance to proteolytic degradation. Examples include fusion proteins. Variant polypeptides can also be referred to herein as "polypeptide analogs." As used herein a "derivative" also refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., Biochem. 32: 1180-1187 (1993); Kobayashi et al., Protein Eng. 12(10):879-884 (1999); and Burks et al., Proc. Natl. Acad. Sci. USA 94:412-417 (1997)).

As used herein, the term "binding molecule" refers in its broadest sense to a molecule that specifically binds an antigenic determinant. As described further herein, a binding molecule can comprise one of more "binding domains." As used herein, a "binding domain" is a two- or three-dimensional polypeptide structure that cans specifically bind a given antigenic determinant, or epitope. A non-limiting example of a binding molecule is an antibody or fragment thereof that comprises a binding domain that specifically binds an antigenic determinant or epitope. Another example of a binding molecule is a bispecific antibody comprising a first binding domain binding to a first epitope, and a second binding domain binding to a second epitope.

Disclosed herein are certain binding molecules, or antigen-binding fragments, variants and/or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

By "specifically binds," it is meant that a binding molecule, e.g., an antibody or antigen-binding fragment thereof binds to an epitope via its antigen binding domain, and that the binding entails some recognition between the antigen binding domain and the epitope. According to this definition, a binding molecule is said to "specifically bind" to an epitope when it binds to that epitope, via its antigen-binding domain binds more readily than it would bind to a random, unrelated epitope.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition, or disorder or those in which the disease, condition or disorder is to be prevented.

The term "pharmaceutical composition" refers to a preparation that is in such form as to permit the biological activity of the active ingredient to be effective and does not contain components that are unacceptably toxic to a subject to which the composition would be administered. Such composition can be sterile.

An "effective amount" as disclosed herein is an amount sufficient to carry out a specifically stated purpose. An "effective amount" can be determined empirically and in a routine manner, in relation to the stated purpose.

"IL12Rβ1" (NP_001276952.1, UniProtKB Identifier P42701) also known as interleukin 12 receptor subunit beta 1, Cluster Of Differentiation 212 (CD212), IMD30, IL12RB, or IL-12R-BETA1. At the transcription level, IL12Rβ1 is encoded by the gene IL12RB1 (for example, the nucleotide sequence identified as NCBI Entrez Gene: 3594). The protein encoded by this gene is a type I transmembrane protein that belongs to the hemopoietin receptor superfamily. This protein binds to interleukin 12 (IL12) and IL23 with a low affinity, and is a part of IL12 receptor and IL23 receptor complex. This protein forms a disulfide-linked oligomer, which is required for its IL12 binding activity. The co-expression of this and IL12RB2 proteins was shown to lead to the formation of high-affinity IL12 binding sites and reconstitution of IL12 dependent signaling. Mutations in this gene impair the development of interleukin-17-producing T lymphocytes and result in increased susceptibility to mycobacterial and *Salmonella* infections. Alternative splicing results in multiple transcript variants. Unless expressly stated otherwise, "IL12Rβ1" refers to "human IL12Rβ1" and includes all transcript variants. "Recombinant IL12Rβ1" refers to IL12Rβ1 encoded by a nucleic acid that has been introduced into a system (e.g. a prokaryotic cell, a eukaryotic cell, or a cell-free expression system) that supports expression of the nucleic acid and its translation into a protein. Methods for producing recombinant proteins are well-known in the art, and the production of recombinant IL12Rβ1 disclosed herein is not limited to a particular system.

The term "antibody," as used herein, is used in the broadest sense and encompasses various antibody and antibody-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alphabodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchangeably, and refer to an antibody having a structure substantially similar to a native antibody structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as compared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), as defined below for various antibodies of this disclosure. Unless otherwise indicated, HVR residues and other residues in the variable domain (e.g., FR residues) are numbered herein according to Kabat et al., supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab, Fab', Fab'-SH, F(ab')$_2$; single-chain forms of antibodies and higher order variants thereof; single-domain antibodies, and multispecific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG domain, such as IgG1, IgG2, IgG3, or IgG4, or a heavy chain constant domain derived from IgA, IgM, or IgE). Diabodies, triabodies, and tetrabodies and higher order variants are typically created by varying the length of the linker peptide from zero to several amino acids. Alternatively, it is also well known in the art that multivalent binding antibody variants can be generated using self-assembling units linked to the variable domain.

An antibody of the disclosure may be a Dual-affinity Re-targeting Antibody (DART). The DART format is based on the diabody format that separates cognate variable domains of heavy and light chains of the 2 antigen binding specificities on 2 separate polypeptide chains. Whereas the 2 polypeptide chains associate noncovalently in the diabody format, the DART format provides additional stabilization through a C-terminal disulfide bridge. DARTs can be produced in high quantity and quality and reveal exceptional stability in both formulation buffer and human serum.

A "single-domain antibody" refers to an antibody fragment consisting of a single, monomeric variable antibody domain.

Multispecific antibodies include bi-specific antibodies, tri-specific, or antibodies of four or more specificities. Multispecific antibodies may be created by combining the heavy and light chains of one antibody with the heavy and light chains of one or more other antibodies. These chains can be covalently linked.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

A "heavy chain antibody" refers to an antibody that consists of two heavy chains. A heavy chain antibody may be an IgG-like antibody from camels, llamas, alpacas, sharks, etc., or an IgNAR from a cartilaginous fish.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germline by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived), e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows, or using similar methods familiar to those with skill in the art (for example, see Almagro, et al. Front. Biosci. 2008, 13(5):1619-33). A murine antibody variable region is aligned to the most similar human germline sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different reversion mutations are generated and empirically tested for activity. The humanized antibody variant with properties most similar to the parent murine antibody and the fewest murine framework reversions is selected as the final humanized antibody candidate.

II. Anti-IL12Rβ1 Antibody

Anti-IL12Rβ1 antibodies disclosed herein can be described or specified in terms of the epitope(s) that they recognize or bind. The portion of a target polypeptide that specifically interacts with the antigen binding domain of an antibody is an "epitope." Furthermore, it should be noted that an "epitope" on IL12Rβ1 can be a linear epitope or a conformational epitope, and in both instances can include non-polypeptide elements, e.g., an epitope can include a carbohydrate or lipid side chain. The term "affinity" refers to a measure of the strength of the binding of an individual epitope with an antibody's antigen binding site.

An "anti-IL12Rβ1 antibody," as used herein, refers to an isolated antibody that binds to recombinant human IL12Rβ1 or IL12Rβ1 isolated from biological sample with an affinity constant or affinity of interaction (KD) between about 0.1 pM to about 10 μM, preferably about 0.1 pM to about 1 μM, more preferably about 0.1 pM to about 100 nM. Methods for determining the affinity of an antibody for an antigen are known in the art. Anti-IL12Rβ1 antibodies useful herein include those which are suitable for administration to a subject in a therapeutic amount.

Anti-IL12Rβ1 antibodies disclosed herein can also be described or specified in terms of their cross-reactivity. The term "cross-reactivity" refers to the ability of an antibody, specific for one antigen, to react with a second antigen; a measure of relatedness between two different antigenic substances. Thus, an antibody is cross-reactive if it binds to an epitope other than the one that induced its formation. The cross-reactive epitope generally contains many of the same complementary structural features as the inducing epitope, and in some cases, can actually fit better than the original. For example, certain antibodies have some degree of cross-reactivity, in that they bind related, but non-identical epitopes, e.g., epitopes with at least about 85%, at least about 90%, or at least about 95% identity (as calculated using methods known in the art) to a reference epitope. An antibody can be said to have little or no cross-reactivity if it does not bind epitopes with less than about 95%, less than about 90%, or less than about 85% identity to a reference epitope. An antibody can be deemed "highly specific" for a certain epitope, if it does not bind any other analog, ortholog, or homolog of that epitope.

Other aspects of anti-IL12Rβ1 antibodies of this disclosure are described more thoroughly below.

In another aspect, an anti-IL12Rβ1 antibody has a heavy chain variable region comprising SEQ ID NO: 3. In some embodiments, the heavy chain variable region further comprises SEQ ID NO: 1 and/or SEQ ID NO: 2. In certain of the above embodiments, the antibody has a light chain variable region comprising SEQ ID NO: 5. The light chain variable region of the above embodiments, can further comprise (a) SEQ ID NO: 4; and/or (b) the amino acid sequence YTS. In another aspect, an anti-IL12Rβ1 antibody has a heavy chain variable region comprising SEQ ID NO: 7. In certain of the above embodiments, the antibody has a light chain variable region comprising SEQ ID NO: 8.

In another aspect, an anti-IL12Rβ1 antibody is selected from Table A.

In an exemplary embodiment, an anti-IL12Rβ1 antibody of this group comprises a VL that has one or more HVRs derived from SEQ ID NO: 7 or a VH that has one or more HVRs derived from SEQ ID NO: 6. The HVR derived from SEQ ID NO: 7 may be L1, L2, L3, or any combination thereof. In certain embodiments, the VL may comprise an L1 of SEQ ID NO: 4, an L2 of YTS, an L3 of SEQ ID NO: 5, or any combination thereof (e.g. antibodies 1-7 in Table A). The HVR derived from SEQ ID NO: 6 may be H1, H2, H3, or any combination thereof. In certain embodiments, the VH may comprise an H1 of SEQ ID NO: 1, an H2 of SEQ ID NO: 2, an H3 of SEQ ID NO: 3, or any combination thereof (e.g. antibodies 8-14 in Table A). In various embodiments above, the antibody may be a humanized antibody, or the antibody may have a VL with 90, 91, 92, 93, 94, 95, 96, 97, 98, 99, or 100% identity to SEQ ID NO: 7 and/or a VH with 90, 91, 92, 93, 94, 95, 96, 97, 98, 99 or 100% identity to SEQ ID NO: 6. In each of the above embodiments, the anti-IL12Rβ1 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 1, 2, 3, 4, 5, 6, or 7, which can readily be determined by one of

TABLE A

| Antibody | Group I antibodies | | | | | |
|---|---|---|---|---|---|---|
| | Light Chain HVR | | | Heavy Chain HVR | | |
| | L1 | L2 | L3 | H1 | H2 | H3 |
| 1 | SEQ ID NO: 4 | | | | | |
| 2 | SEQ ID NO: 4 | YTS | | | | |
| 3 | SEQ ID NO: 4 | YTS | SEQ ID NO: 5 | | | |
| 4 | | YTS | | | | |
| 5 | | YTS | SEQ ID NO: 5 | | | |
| 6 | | | SEQ ID NO: 5 | | | |
| 7 | SEQ ID NO: 4 | | SEQ ID NO: 5 | | | |
| 8 | | | | SEQ ID NO: 1 | | |
| 9 | | | | SEQ ID NO: 1 | SEQ ID NO: 2 | |
| 10 | | | | SEQ ID NO: 1 | SEQ ID NO: 2 | SEQ ID NO: 3 |
| 11 | | | | | SEQ ID NO: 2 | |
| 12 | | | | | SEQ ID NO: 2 | SEQ ID NO: 3 |
| 13 | | | | | | SEQ ID NO: 3 |
| 14 | | | | SEQ ID NO: 1 | | SEQ ID NO: 3 |
| 15 | SEQ ID NO: 4 | | | SEQ ID NO: 1 | | |
| 16 | SEQ ID NO: 4 | | | SEQ ID NO: 1 | SEQ ID NO: 2 | |
| 17 | SEQ ID NO: 4 | | | SEQ ID NO: 1 | SEQ ID NO: 2 | SEQ ID NO: 3 |
| 18 | SEQ ID NO: 4 | | | | SEQ ID NO: 2 | |
| 19 | SEQ ID NO: 4 | | | | SEQ ID NO: 2 | SEQ ID NO: 3 |
| 20 | SEQ ID NO: 4 | | | | | SEQ ID NO: 3 |
| 21 | SEQ ID NO: 4 | | | SEQ ID NO: 1 | | SEQ ID NO: 3 |
| 22 | SEQ ID NO: 4 | YTS | | SEQ ID NO: 1 | | |
| 23 | SEQ ID NO: 4 | YTS | | SEQ ID NO: 1 | SEQ ID NO: 2 | |
| 24 | SEQ ID NO: 4 | YTS | | SEQ ID NO: 1 | SEQ ID NO: 2 | SEQ ID NO: 3 |
| 25 | SEQ ID NO: 4 | YTS | | | SEQ ID NO: 2 | |
| 26 | SEQ ID NO: 4 | YTS | | | SEQ ID NO: 2 | SEQ ID NO: 3 |
| 27 | SEQ ID NO: 4 | YTS | | | | SEQ ID NO: 3 |
| 28 | SEQ ID NO: 4 | YTS | | SEQ ID NO: 1 | | SEQ ID NO: 3 |
| 29 | SEQ ID NO: 4 | YTS | SEQ ID NO: 5 | SEQ ID NO: 1 | | |
| 30 | SEQ ID NO: 4 | YTS | SEQ ID NO: 5 | SEQ ID NO: 1 | SEQ ID NO: 2 | |
| 31 | SEQ ID NO: 4 | YTS | SEQ ID NO: 5 | SEQ ID NO: 1 | SEQ ID NO: 2 | SEQ ID NO: 3 | skill in the art, and may be incorporated into a vector or other large DNA molecule, such as a chromosome (e.g. incorporated into the genome of a host cell), in order to express an antibody of the disclosure. In an exemplary embodiment, a nucleic acid sequence of the disclosure comprises SEQ ID NO: 8 and/or 9.

In some embodiments, the isolated antibody according to the disclosure may be a fully human or humanized antibody. In one embodiment, it comprises a mutant or chemically modified amino acid Fc region, wherein said mutant or chemical modification confers no or decreased ADCC activity to said antibody when compared to a corresponding antibody with wild type Fc region. In a specific embodiment, it is a mutant silent IgG1 antibody.

III. Treatment Methods

The present disclosure provides methods for the use of an antibody of this disclosure, to treat, reduce, or prevent a disease associated with inflammation or an immune response. For example, a disease or condition associated with inflammation or an immune response can include those associated with IL12 receptor signaling and/or IL23 receptor signaling. Methods are provided for the use of an antibody of this disclosure, to treat subjects, for example as a means of disease prevention, treatment, and management and according for example, to any of the following. In some embodiments, an antibody of the disclosure is a IL12 and/or IL23 receptor antagonist capable of inhibiting IL12 and/or IL23 receptor induced cytokine production and/or IL12 and/or IL23 receptor induced activation of blood cells to treat pathological disorders, such as rheumatoid arthritis, psoriasis or inflammatory bowel diseases or other autoimmune and inflammatory disorders. Suitable anti-IL12Rβ1 antibodies are described in Section II. In embodiments where the subject is a human, the anti-IL12Rβ1 antibody is adapted for administration to a living human subject (e.g. humanized).

In one embodiment, the disclosure provides a method of preventing the progression, or slowing the rate of progression, or ameliorating an autoimmune and/or inflammatory disease. The method comprises administering a therapeutically effective amount of an anti-IL12Rβ1 antibody to a subject in need thereof. Suitable anti-IL12Rβ1 antibodies include those disclosed herein. Progression of a disease can be evaluated by methods known in the art and described herein, including a worsening of a clinical sign of an autoimmune and/or inflammatory disease, or a symptom associated with an autoimmune and/or inflammatory disease. In exemplary embodiments, the clinical sign is IL12 and/or IL23 receptor induced cytokine production and/or IL12 and/or IL23 receptor induced immune cell activation.

This gene encodes a subunit of interleukin 12, a cytokine that acts on T and natural killer cells, and has a broad array of biological activities. Interleukin 12 is a disulfide-linked heterodimer composed of the 40 kD cytokine receptor like subunit encoded by the IL12B gene, and a 35 kD subunit encoded by the IL12A gene. This cytokine is expressed by activated macrophages and dendritic cells that serve as an essential inducer of Th1 cells development. This cytokine has been found to be important for sustaining a sufficient number of memory/effector Th1 cells to mediate long-term protection to an intracellular pathogen. Overexpression of this gene was observed in the central nervous system of patients with multiple sclerosis (MS), suggesting a role of this cytokine in the pathogenesis of the disease. The promoter DNA polymorphism of this gene has been reported to be associated with the severity of atopic and non-atopic asthma in children.

Interleukin 12 (IL-12) is an interleukin that is naturally produced by dendritic cells, macrophages, neutrophils, and human B-lymphoblastoid cells (NC-37) in response to antigenic stimulation. IL-12 is composed of a bundle of four alpha helices. It is a heterodimeric cytokine encoded by two separate genes, IL-12A (p35) and IL-12B (p40). The active heterodimer (referred to as 'p70'), and a homodimer of p40 are formed following protein synthesis.

IL-12 is linked with autoimmunity. Administration of IL-12 to people suffering from autoimmune diseases was shown to worsen the autoimmune phenomena. This is believed to be due to its key role in induction of Th1 immune responses. In contrast, IL-12 gene knock-out in mice or a treatment of mice with IL-12 specific antibodies ameliorated the disease. Interleukin 12 (IL-12) is produced by activated antigen-presenting cells (dendritic cells, macrophages). It promotes the development of Th1 responses and is a powerful inducer of IFNγ production by T and NK cells. Other diseases associated with IL12B include Immunodeficiency, Mycobacteriosis and Familial Atypical Mycobacteriosis. IL-12p70 has been shown to be overexpressed in Crohn's disease. Dysregulated expression of IL-12 p40 can lead to prolonged, unresolved inflammation manifesting into chronic inflammatory disorders such as inflammatory bowel disease (IBD). Overexpression IL12B was observed in the central nervous system of patients with multiple sclerosis (MS). Diseases associated with IL12RB1 include Immunodeficiency and Familial Atypical Mycobacteriosis.

IL-23 is produced by macrophages and dendritic cells and determines the development of IL-17-producing T helper (TH17) cells. IL-23 is related to IL-12. IL-23 shares the IL-12p40 subunit with IL-12 but only IL-23 uses the p19 subunit. Mice deficient in IL-23 are resistant to experimental immune-mediated disease. Therapeutic agents targeting IL-23 or IL-17 are used in the clinic for many immune-mediated diseases. IL-23 transmits intracellular signals through a receptor consisting of two subunits, IL-23R and IL-12Rβ1. IL-23R is used solely by IL-23, whereas IL-12Rβ1 is shared with IL-12. IL-23R/IL-12Rβ1 activates STAT3 predominantly. IL-12Rβ2/IL-12Rβ1 activates preferentially STAT4. Thus, the difference between IL-12- and IL-23-dependent signaling is due in part to the preferential activation of STAT4-dependent target genes by IL-12 and of STAT3-dependent target genes by IL-23. While IL-12 promotes the development of TH1, which produce IFN-γ, IL-23 promotes TH17 cells, which produce IL-17A and IL-17F. IL-17 and IL-23 provide protection against extracellular bacterial and fungal infections, but inappropriate production can cause autoimmune diseases, such as psoriasis, arthritis and other inflammatory diseases. Thus, dysregulated production of IFN-γ and/or IL-17A and/or IL-17F provide a rationale for targeting IL-12Rβ1 for inflammatory disorders.

In another embodiments, the present disclosure provides a method for preventing, treating, and managing an autoimmune and/or inflammatory disease in a human subject, the method comprising administering to a human in need thereof an effective amount of the antibody or a composition of this disclosure. In certain embodiments, the antibody is co-administered with one or more additional therapeutic agent. In certain embodiments, the co-administration enhances the anti-inflammatory therapy in the subject.

Antibody compositions of the present disclosure can further comprise at least one of any suitable and effective amount of a composition or pharmaceutical composition comprising at least one anti-IL12Rβ1 antibody to a cell, tissue, organ, animal or subject in need of such modulation, treatment or therapy, optionally further comprising at least one additional therapeutic agent selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic. a neuromuscular blocker, an antimicrobial (e.g., ammoglycoside, an antifungal, an antiparasitic. an antiviral, a carbapenem, cephalosporin. a flurorquinolone, a macrohde, a penicillin, a sulfonamide, a tetracyclme, another antimicrobial), an antipsoiratic, a corticosteroid, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitm (e g., epoetin alpha), a filgrastim (e.g., G-CSF, Neupogen), a sargramostim (GM-CSF, Leukine), an immunization, an immunoglobulin, an immunosuppressive (e g., basihximab, cyclosporine, dachzumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimamc agent, an antipsychotic, an anxiolytic, a hypnotic, a sympathomimetic, a stimulant, donepezil, tacrrne, an asthma medication, a beta agonist, an inhaled steroid, a leukotrrene inhibitor, a methylxanthme, a cromolyn, an epinephrine or analog, domase alpha (Pulmozyme), a cytokine or a cytokine antagonist. Non-limiting examples of such cytokines include, but are not limited to, any of IL-12 to IL-23. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference. In some embodiments, an anti-IL12Rβ1 antibody of the disclosure may be an alternative therapeutic to Ustekinumab or used in combination with Ustekinumab and provide more advantageous properties due to the observation that the pathogenic T helper cells express high levels of IL12Rβ1 suggesting these cells might be preferentially targeted by an antibody of the disclosure.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one or more of diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios* par ahemolyticus), *Klebsiella* species, *Pseudomonas aeruginosa*, and Streptococci. See, e.g., Stein, ed., INTERNAL MEDICINE, 3rd ed., pp 1-13, Little, Brown and Co., Boston, (1990); Evans et al., eds., Bacterral Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone. N.Y. (1990); Berkow et al, eds., The Merck Manual, 16th edition, Merck and Co., Rahway, N.J., 1992; Wood et al, FEMS Microbiology Immunology, 76: 121-134 (1991); Marrack et al, Science, 248:705-711 (1990), the contents of which references are incorporated entirely herein by reference. In one embodiment, the inflammatory disease is not a microbial infection.

A single therapeutic antibody can be developed into several different therapeutic agents and certain embodiments include, in non-limiting examples, antibody-drug conjugates, antibody-radio conjugates, bispecific antibodies, fusion antibodies, CART cells, immunotoxins, DARTs, and other agents.

In certain embodiments, antibody drug conjugates (ADCs) are used to deliver cytotoxic drugs specifically to cancer. There are three components to ADCs: antibody, drug and linker. Linkers are used to conjugate the drug to the antibody. Following endocytosis, the drug dissociates from the antibody and initiates cytotoxicity.

In certain of any of the treatment, prevention, and management embodiments of this disclosure, the antibody or antigen-binding fragment is conjugated to a therapeutic agent, a protein, a lipid, a detectable label, and/or a polymer, or any combination thereof.

The present disclosure also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy. organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference. The present invention also provides a method for modulating or treating at least one cardiovascular disease in a cell, tissue, organ, animal, or subject.

In some embodiments, diseases and disorders that can be treated by the antibodies of the present disclosure include but are not limited to adult and juvenile Still disease; asthma; allergy; Alzheimer's disease; age-related macular degeneration; antisynthetase syndrome; autoinflammatory disease; autoimmune disease; autoimmune response; Behçet disease; Blau syndrome; cancer; cardiovascular infarction; chronic infantile neurological cutaneous and articular (CINCA) syndrome; chronic recurrent multifocal osteomyelitis; cinca syndrome; classic autoinflammatory diseases; cryopyrin-associated autoinflammatory syndromes (CAPS); deficiency in IL-1 receptor antagonist (DIRA); diabetes mellitus; Erdheim-Chester disease (histiocytosis); extrapulmonary tuberculosis; familial atypical mycobacteriosis; familial cold autoinflammatory syndrome (FCAS); gastric cancer Risk after *H. pylori* Infection; Guillain-Barré syndrome; Hashimoto's thyroiditis; heart failure; hepatic fibrosis; Huntington's disease; hyper IgD syndrome (HIDS); hypoxia; ischaemia-reperfusion; immunodeficiency 29; inflammation; inflammation by HIV; inflammatory bowel disease (IBD); macrophage activation syndrome (MAS); mycobacteriosis; Miller-Fisher syndrome; Muckle-Wells syndrome (MWS); multiple sclerosis (MS); neonatal-onset multisystem inflammatory disease (NOMID); neuropathic pain; N syndrome; osteoarthritis; osteoporosis; Periodontal Disease; periodic fever, aphthous stomatitis, pharyngitis, adenitis syndrome (PFAPA); postmyocardial infarction heart failure; psoriasis; recurrent idiopathic pericarditis; recurrent pericarditis; relapsing chondritis; relapsing-remitting multiple sclerosis; rheumatoid arthritis (RA); Sapho Syndrome; Schnitzler syndrome; secondary progressive multiple sclerosis; septic shock; smoldering myeloma; Sweet syndrome; synovitis, acne, pustulosis, hyperostosis, osteitis (SAPHO); systemic juvenile rheumatoid arthritis; familial Mediterranean fever (FMF); pyogenic arthritis; pyoderma gangrenosum, acne (PAPA); TNF receptor-associated periodic syndrome (TRAPS); type 2 diabetes; urate crystal arthritis (gout); or urticarial vasculitis.

For each of the above embodiments, suitable anti-IL12Rβ1 antibodies are described in Section II.

As discussed above, an anti-IL12Rβ1 antibody disclosed herein can also be conjugated to therapeutic agents, prodrugs, peptides, proteins, enzymes, viruses, biological response modifiers, pharmaceutical agents, nanoparticles or PEG. In certain embodiments, therapeutic agent may be a drug, a radioisotope, a lectin, or a toxin. Conjugates that are immunotoxins have been widely described in the art. The toxins can be coupled to the antibodies by conventional coupling techniques or immunotoxins containing protein toxin portions can be produced as fusion proteins. Other therapeutic agents which can be coupled to the anti-IL12Rβ1 antibodies, as well as ex vivo and in vivo therapeutic protocols, are known, or can be easily ascertained, by those of ordinary skill in the art.

Administration is performed using standard effective techniques, including peripherally or locally. Peripheral administration includes but is not limited to intravenous, intraperitoneal, subcutaneous, pulmonary, transdermal, intramuscular, intranasal, buccal, sublingual, or suppository administration. Local administration includes administration directly into an anatomical site of interest, for example, administration directly into the central nervous system (CNS) which includes but is not limited to via a lumbar, intraventricular or intraparenchymal catheter or using a surgically implanted controlled release formulation. In some embodiments, the antigen binding peptides as disclosed herein are used in combination with focused ultrasound. Focused ultrasound is an early-stage, non-invasive therapeutic technology with the potential to transform the treatment of many medical disorders by using ultrasonic energy to target tissue deep in the body without incisions or radiation. High-intensity focused ultrasound (HIFU) is a non-invasive therapeutic technique that uses non-ionizing ultrasonic waves to heat tissue. HIFU can be used to increase the flow of blood or lymph, or to destroy tissue, such as tumors, through several mechanisms. HIFU may be combined with other imaging techniques such as medical ultrasound or MRI to enable guidance of the treatment and monitoring.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living subject could be made up to contain 1 mL sterile buffered water of phosphate buffered saline and about 1-1000 mg of any one of or a combination of the antibodies disclosed herein. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-IL12Rβ1 antibody concentration. Anti-IL12Rβ1 antibodies disclosed herein can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the subject when administered. Generally, a pH between 4 and 8 is tolerated. Doses will vary from individual to individual based on size, weight, and other physiobiological characteristics of the individual receiving the successful administration.

As used herein, the term "therapeutically effective amount" means an amount of a substance (e.g. an anti-IL12Rβ1 antibody) that leads to measurable and beneficial effects for the subject administered the substance, i.e., significant efficacy. The therapeutically effective amount or dose of compound administered according to this discovery will be determined using standard clinical techniques and may be by influenced by the circumstances surrounding the case, including the antibody administered, the route of administration, and the status of the symptoms being treated, among other considerations. A typical dose may contain from about 0.01 mg/kg to about 100 mg/kg of an anti-IL12Rβ1 antibody described herein. Doses can range from about 0.05 mg/kg to about 50 mg/kg, more preferably from about 0.1 mg/kg to about 25 mg/kg. The frequency of dosing may be daily or once, twice, three times or more per week or per month, as needed as to effectively treat the symptoms.

The timing of administration of the treatment relative to the disease itself and duration of treatment will be determined by the circumstances surrounding the case. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein. In addition, a person skilled in the art can use a polynucleotide of the invention encoding any one of the above-described antibodies instead of the proteinaceous material itself. For example, In addition, it may be desirable to employ controlled release formulations using biodegradable films and matrices, or osmotic mini-pumps, or delivery systems based on dextran beads, alginate, or collagen.

IV. Pharmaceutical Compositions

The present disclosure encompasses pharmaceutical compositions comprising an anti-IL12Rβ1 antibody disclosed in Section II, so as to facilitate administration and promote stability of the active agent. For example, an anti-IL12Rβ1 antibody of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). Methods of preparing and administering anti-IL12Rβ1 antibodies disclosed herein to a subject in need thereof are well known to or are readily determined by those skilled in the art. The route of administration of an anti-IL12Rβ1 antibody can be, for example, peripheral, oral, parenteral, by inhalation or topical.

Pharmaceutical compositions for effective administration are deliberately designed to be appropriate for the selected mode of administration, and pharmaceutically acceptable excipients such as compatible carriers, dispersing agents, buffers, surfactants, preservatives, solubilizing agents, isotonicity agents, stabilizing agents and the like are used as appropriate.

Non-limiting examples of pharmaceutically acceptable carriers, include physiological saline, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat or combination thereof.

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols, such as mannitol, sorbitol, or sodium chloride in the composition.

Prolonged absorption of the injectable compositions can be brought about by including in the composition an agent which delays absorption, for example, aluminum monostearate and gelatin.

Compositions disclosed herein can be frozen or lyophilized for storage and reconstituted in a suitable sterile carrier prior to use.

In some embodiments, anti-IL12Rβ1 antibodies may be formulated for parenteral administration. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions, as disclosed herein, can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-IL12Rβ1 antibody to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Screening of Anti-Human IL-12Rβ1 Hybridomas

Both IL-12 and IL-23 have been implicated in the generation of the pathogenic T helper cells that orchestrate tissue inflammation in the most common autoimmune diseases. The IL12/IL-23 signaling pathway has been associated with the pathogenesis of several inflammatory autoimmune diseases such as Crohn's, ulcelative colitis, rheumatoid arthritis and psoriasis, among others. The use of monoclonal antibodies targeting this pathway has recently emerged as an alternative to treat autoimmune patients and it has shown to provide significant improvement in the clinic and life quality of patients.

Recently, Ustekinumab, a monoclonal antibody (mab) that targets the p40 subunit of both IL-12 and IL-23 has been approved by the FDA for the treatment of plaque psoriasis, psoriatic arthritis and Crohn's disease. Therefore, concomitant inhibition of these cytokines is desirable for the therapy.

Figure 2:
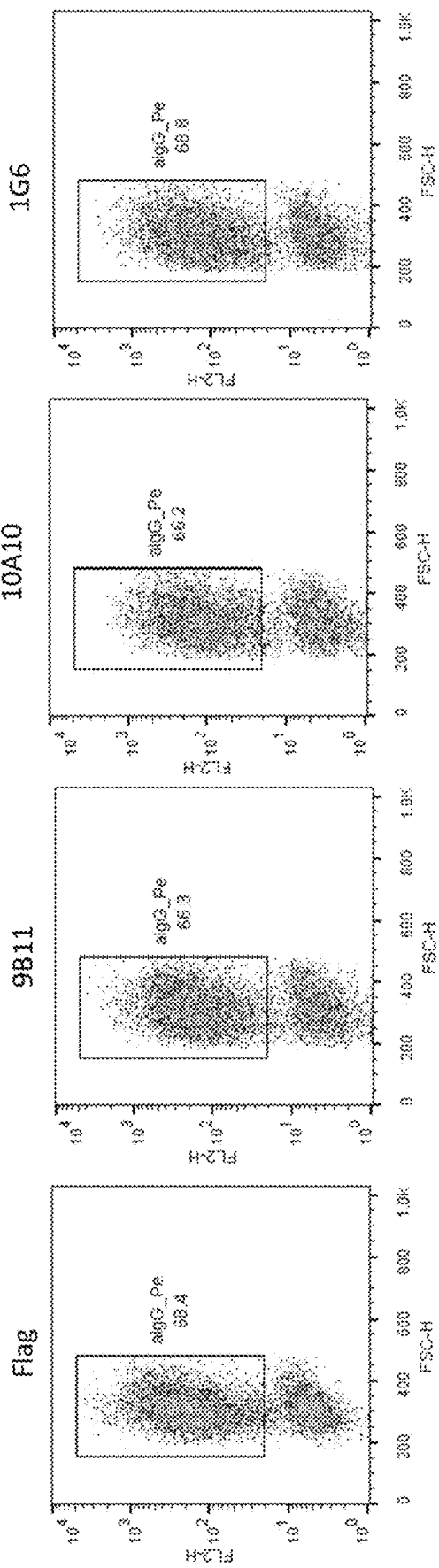
FIG. 2 shows flow cytometry of EL-4 cells transduced with a construct encoding the human IL12Rβ1 and stained with different hybridoma clones.
Figure 3:
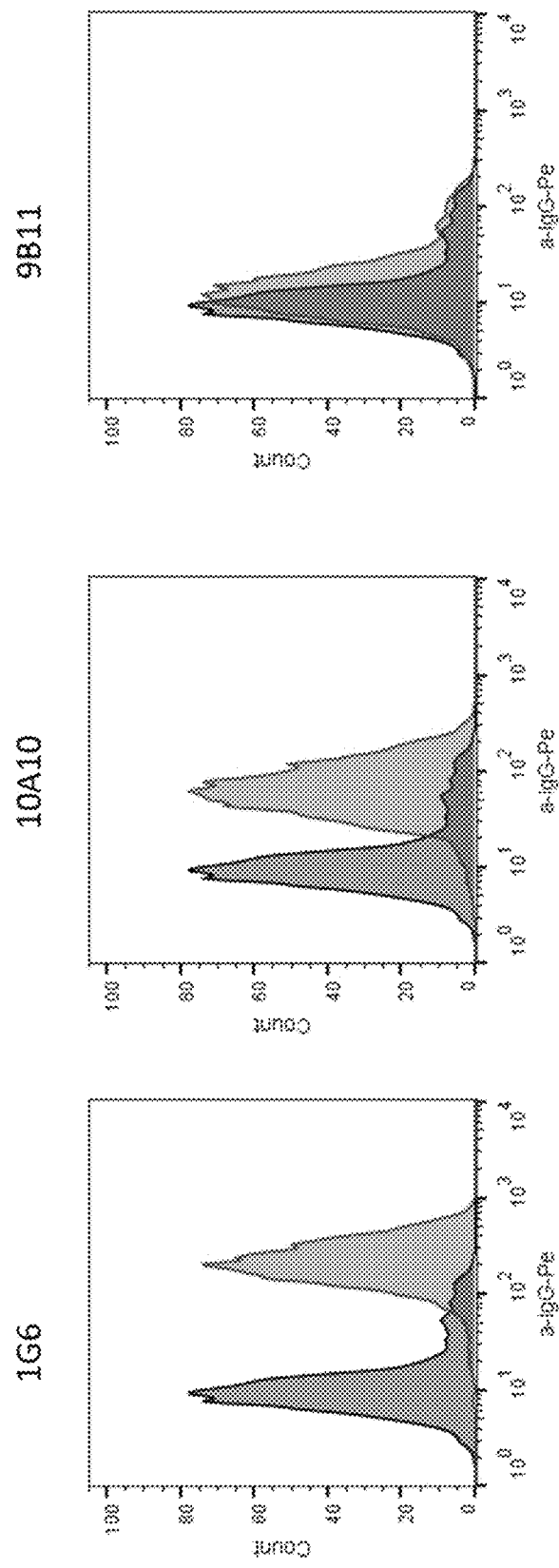
FIG. 3 shows the staining of human primary cells by 1 G6.
Figure 4:
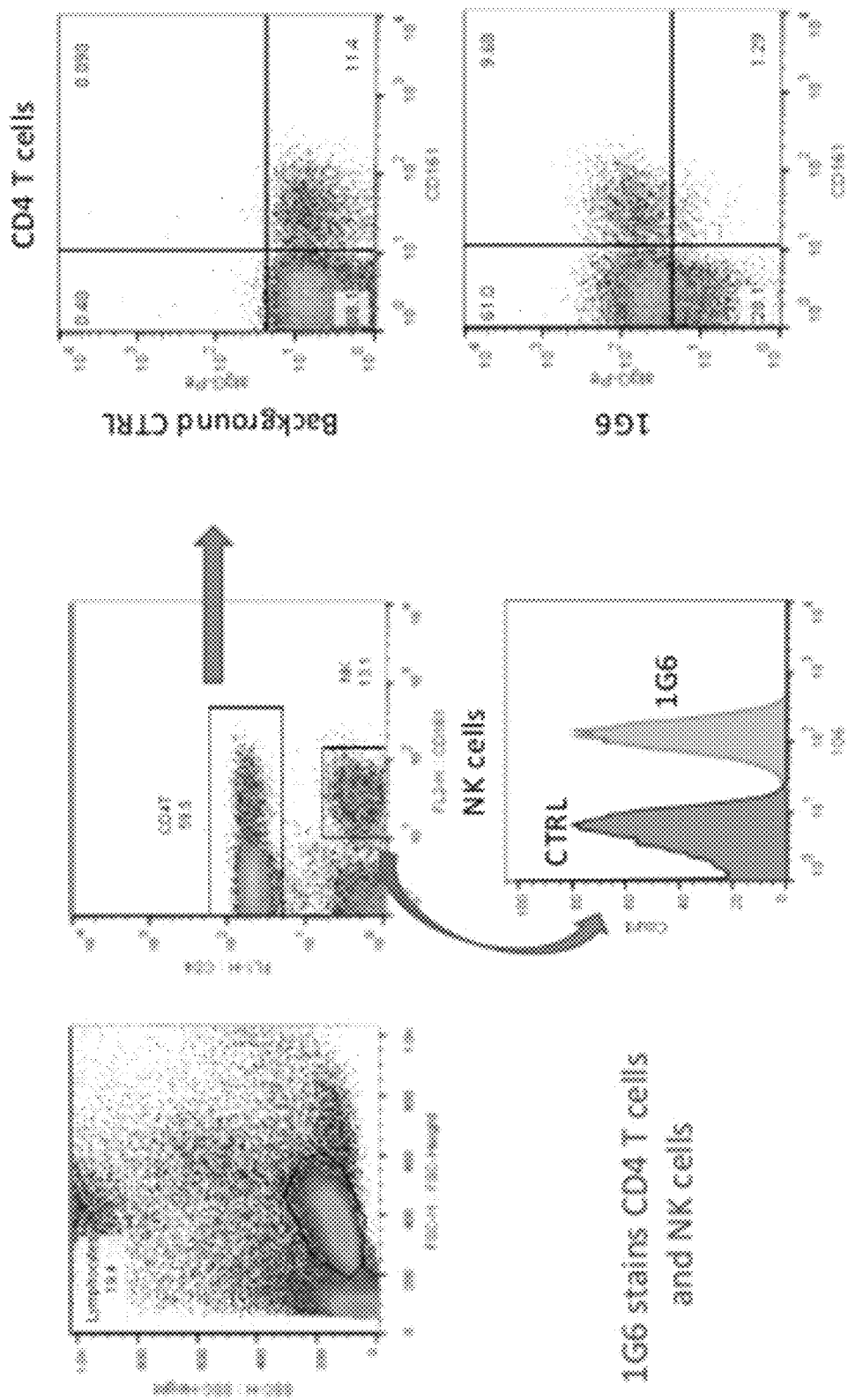
FIG. 4 shows the staining of peripheral blood cells with 1 G6.
Figure 5:
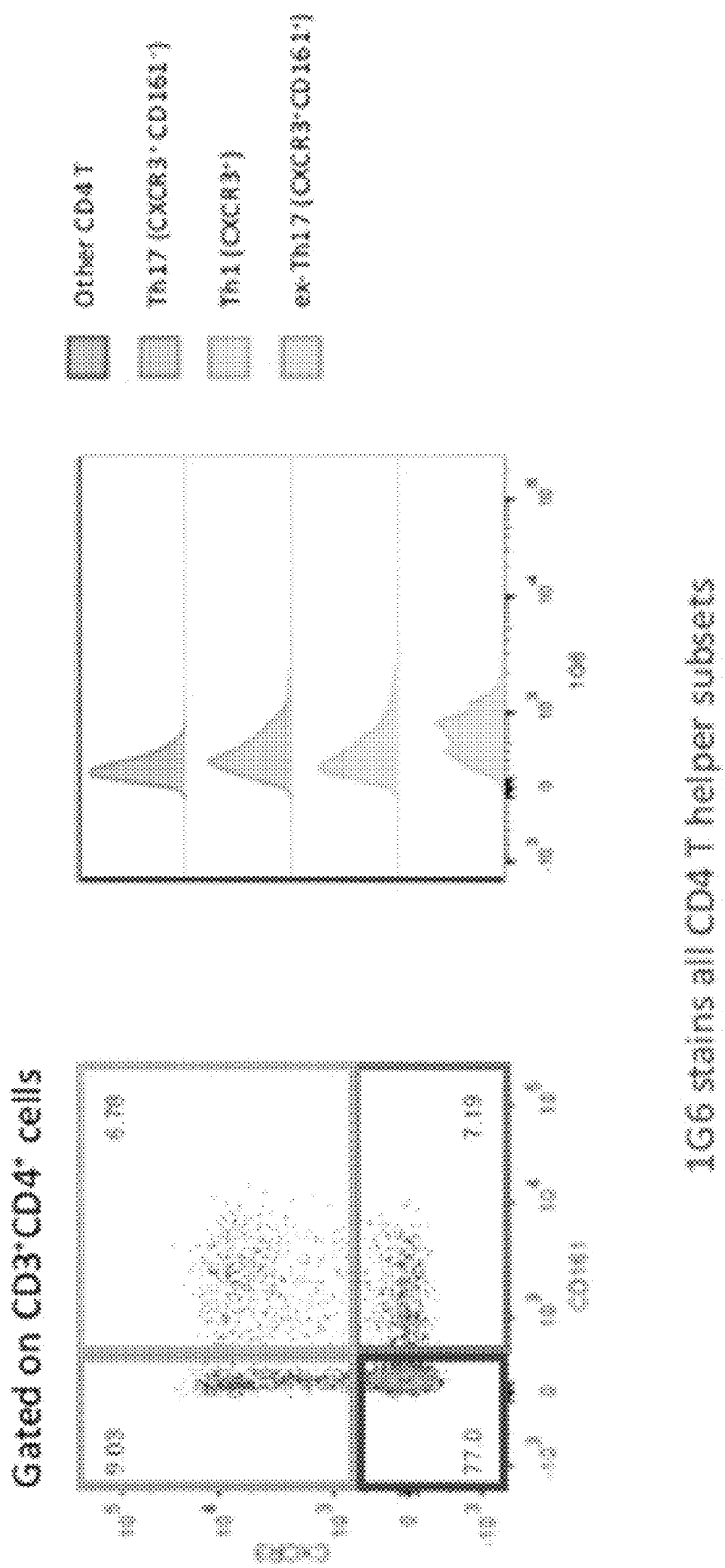
FIG. 5 shows peripheral blood CD4 T subsets stained with biotinylated 1G6.
Figure 6:
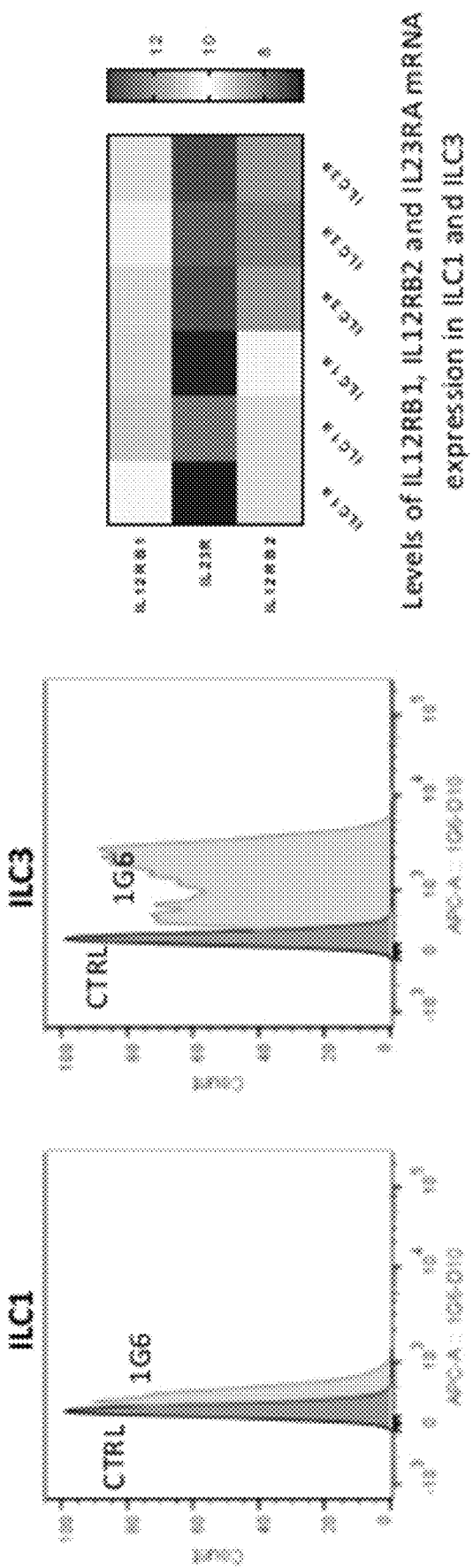
FIG. 6 shows staining of tonsil ILC1 and ILC3 with biotinylated 1G6 and levels of IL12Rβ1, IL12Rβ2 and IL23RA mRNA.

EL-4-human IL-12Rβ1 cell line: The EL-4 cell line was transduced with a construct encoding the human FLAG-tagged IL12Rβ1 Flow cytometry: EL-4-human IL-12Rβ1 cells were stained with supernatants from different hybridoma clones followed by anti-mouse IgG Pe. Staining was compared with that obtained with anti-FLAG Tag followed by anti-mouse IgG Pe. Hybridoma clones staining the same percentage of cells stained by anti-FLAG Tag were selected and further tested in primary cells (FIG. 2).

Further staining of human primary cells by IG6: -ILC3 sort-purified from human tonsils; -NK cells from human peripheral blood (gates: Lymphocyte sized, CD4-CD161+); -Th17, from peripheral blood (gates: Lymphocyte sized, CD4+CD161+); -CD8 T cells from peripheral blood (gates: Lymphocyte sized, CD3+CD8+); Cells were labeled with 1 G6 followed by anti-mouse IgG Pe and then labeled with commercial mAb cocktails for surface staining (i.e. CD3; CD4; CD161; CD8). Each step was carried out at +4 C for 20 min and cells were washed between all steps. Alternatively; biotinylated 1 G6 was used followed by Pe-Cy7 SVD labeling (FIG. 3-FIG. 7).

Figure 7:
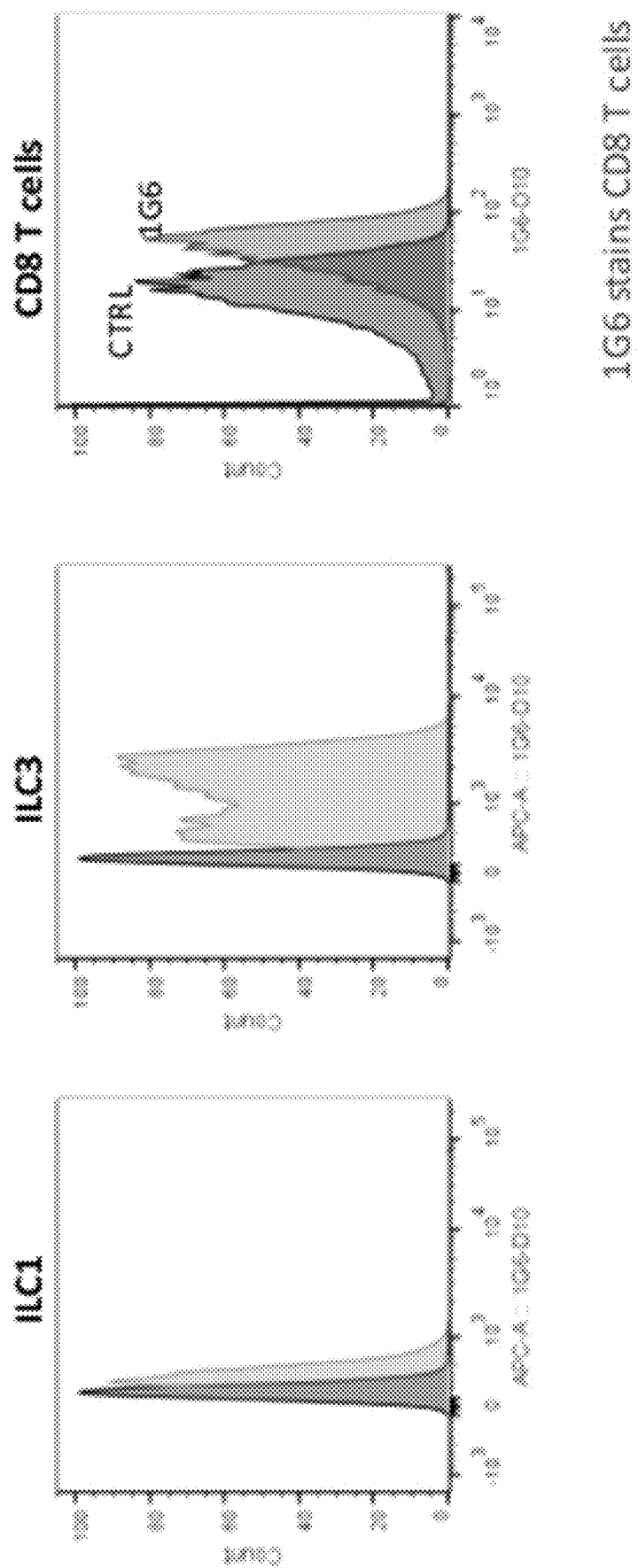
FIG. 7 shows staining of human CD8 T cells with biotinylated 1G6.
Figure 8:
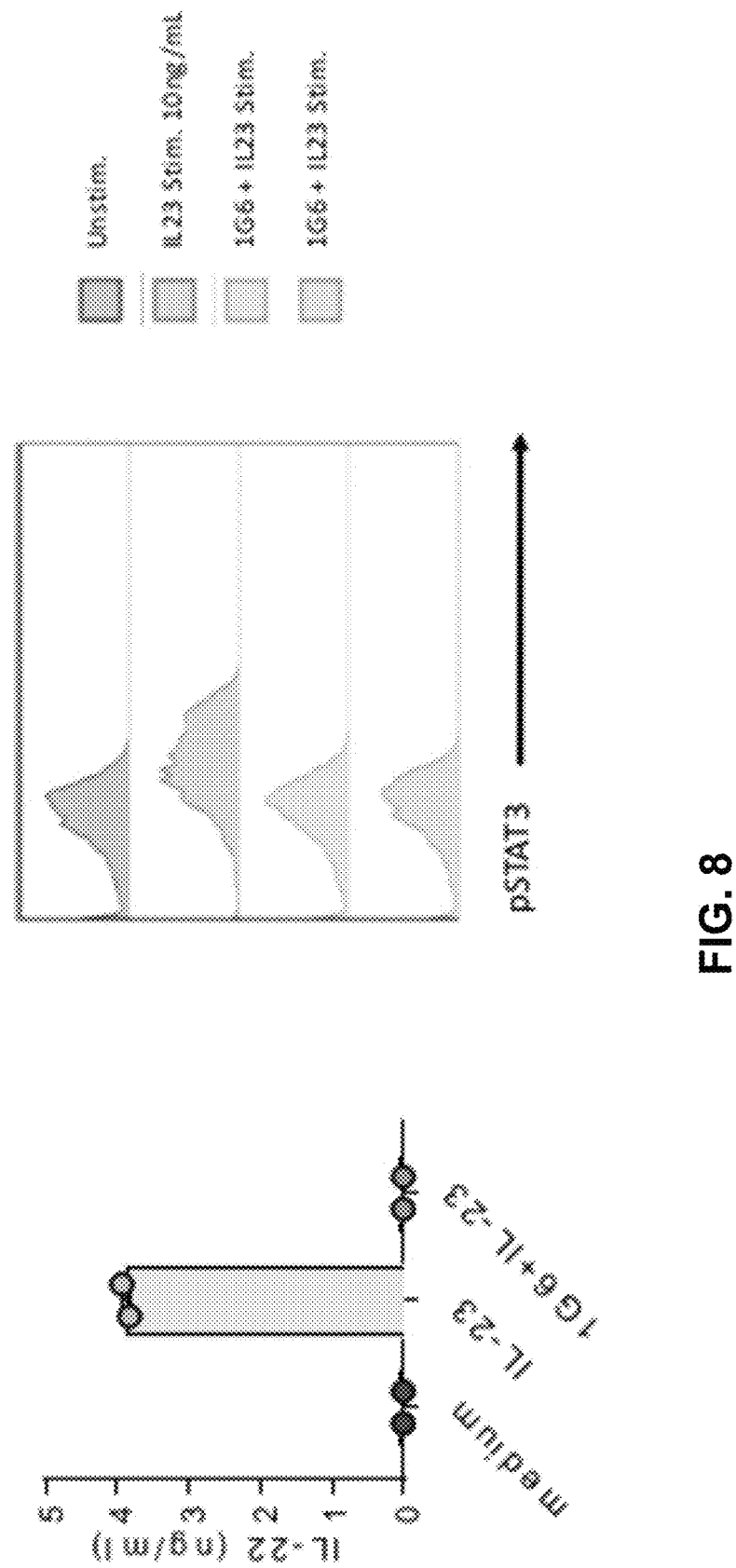
FIG. 8 shows pretreatment of human ILC3s with 1G6 prevented STAT3 phosphorylation induced by IL-23 stimulation.

Blocking experiments: ILC3 sort-purified from human tonsils were pre-incubated with hybridoma supernatants for 20 min at +4 C and then stimulated by adding recombinant human IL-23 (10 ng/mL) to culture medium. Stimulations were carried out at 37 C. After a short stimulation (15 min), cells were fixed, permeabilized and stained for pSTAT3. After a long stimulation (24 h), IL-22 secreted by cells in the culture supernatant was analyzed by ELISA. Results: By staining assays, we selected three hybridoma clones: 1G6 (high staining), 10A10 (high staining), 9B11 (lo staining) By blocking assays we further selected 1 G6 (optimal blocking), whereas 10A10 was de-prioritized because of lack of blocking effect (FIG. 7).

A mab (1 G6) has been generated that binds with high affinity the IL12Rβ1, a common chain shared between IL-12R and IL-23R. IL12Rβ1 is essential for both IL-12 and IL-23 signaling and 1G6 was capable to completely abrogate IL-23 activation of human innate lymphocytes expressing the IL-23R in vitro. There are no high affinity mabs that block the receptors for IL-12 and IL-23, possibly due to the complexity of the receptor structure which makes the generation of such mabs much more difficult than the generation of mabs against the cytokines. 1 G6 may be an alternative to Ustekinumab in the therapy and could potentially provide more advantageous since we have observed that the pathogenic T helper cells express high levels of IL12Rβ1 suggesting these cells might be preferentially targeted by our mab.

SEQUENCE LISTING

<160> NUMBER OF SEQ ID NOS: 9

<210> SEQ ID NO 1
<211> LENGTH: 8
<212> TYPE: PRT
<213> ORGANISM: Artificial Sequence
<220> FEATURE:
<223> OTHER INFORMATION: Synthesized

<400> SEQUENCE: 1

Gly Tyr Thr Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Synthesized

<400> SEQUENCE: 2

Ile Asp Pro Asn Asn Gly Tyr Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

Val Arg Gly Gly Glu Ile Tyr Tyr Phe Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthesized

<400> SEQUENCE: 4

Gln Asp Ile Tyr Lys Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Leu Gln Tyr Asp Asn Ile Leu Trp Thr
1               5

<210> SEQ ID NO 6
<211> LENGTH: 210
<212> TYPE: PRT
<213> ORGANISM: Artificial Sequence
<220> FEATURE:
<223> OTHER INFORMATION: Synthesized

<400> SEQUENCE: 6

Met Glu Arg His Trp Ile Phe Leu Ser Leu Leu Ser Val Ile Ala Gly
1               5                   10                  15

-continued

Val His Ser Arg Val Gln Leu Gln Gln Ser Gly Ala Glu Leu Ala Lys
         20                  25                  30

Pro Gly Ala Ser Val Arg Leu Ser Cys Met Ala Ser Gly Tyr Thr Phe
     35                  40                  45

Thr Ser Tyr Trp Met His Trp Val Lys Gln Arg Pro Gly Gln Gly Leu
 50                  55                  60

Glu Trp Ile Gly Tyr Ile Asp Pro Asn Asn Gly Tyr Thr Lys Tyr Ser
 65                  70                  75                  80

Gln Lys Phe Lys Asp Lys Ala Thr Leu Thr Ala Asp Lys Ser Ser Ser
             85                  90                  95

Thr Ala Asn Met Arg Leu Ser Ser Leu Thr Tyr Glu Asp Ser Ala Val
            100                 105                 110

Tyr Tyr Cys Val Arg Gly Gly Glu Ile Tyr Tyr Phe Asp Tyr Trp Gly
            115                 120                 125

Gln Gly Thr Thr Leu Thr Val Ser Ser Ala Lys Thr Thr Pro Pro Ser
        130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

Thr Trp Asn Ser Gly Ser Leu Ser Ser Val His Thr Phe Pro Ala
            180                 185                 190

Leu Leu Gln Ser Gly Leu Tyr Thr Met Ser Ser Ser Val Thr Val Pro
            195                 200                 205

Ser Ser
    210

<210> SEQ ID NO 7
<211> LENGTH: 203
<212> TYPE: PRT
<213> ORGANISM: Artificial Sequence
<220> FEATURE:
<223> OTHER INFORMATION: Synthesized

<400> SEQUENCE: 7

Met Arg Pro Ser Ile Gln Phe Leu Gly Leu Leu Leu Phe Trp Leu His
 1               5                  10                  15

Gly Gly Gln Cys Asp Ile Gln Met Thr Gln Ser Pro Ser Ser Leu Ser
             20                  25                  30

Ala Ser Leu Gly Gly Lys Val Thr Ile Thr Cys Lys Ala Ser Gln Asp
         35                  40                  45

Ile Tyr Lys Tyr Ile Ala Trp Tyr Gln His Lys Pro Gly Lys Gly Pro
 50                  55                  60

Arg Leu Leu Ile His Tyr Thr Ser Thr Leu Gln Pro Gly Ile Pro Ser
 65                  70                  75                  80

Arg Phe Ser Gly Ser Gly Ser Gly Arg Asp Tyr Ser Phe Ser Ile Ser
             85                  90                  95

Asp Leu Glu Pro Glu Asp Ile Ala Thr Tyr Tyr Cys Leu Gln Tyr Asp
            100                 105                 110

Asn Ile Leu Trp Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

```
Pro Lys Asp Ile Asn Val Lys Trp Lys Ile Asp Gly Ser Glu Arg Gln
             165                 170                 175

Asn Gly Val Leu Asn Ser Trp Thr Asp Gln Asp Ser Lys Asp Ser Thr
        180                 185                 190

Tyr Ser Met Ser Ser Thr Leu Thr Leu Thr Lys
        195                 200
```

```
<210> SEQ ID NO 8
<211> LENGTH: 630
<212> TYPE: DNA
<213> ORGANISM: Artificial Sequence
<220> FEATURE:
<223> OTHER INFORMATION: Synthesized

<400> SEQUENCE: 8
atggaaaggc actggatctt tctctccctg ttgtcagtaa tagcaggtgt ccactcccgg      60
gtccagctgc agcagtccgg ggctgaactg gcaaaacctg gggcctccgt gaggctgtcc     120
tgcatggctt ctggctacac ctttaccagc tactggatgc actgggtaaa acagaggcct     180
ggacagggtc tggaatggat tggatacatt gatcctaaca atggttatac taagtacagt     240
cagaagttca aggacaaggc cacattgact gcagacaaat cctccagcac agccaatatg     300
cggctgagca gcctgacata tgaggactct gcagtctatt actgtgtaag gggggggagag     360 atttactact ttgactactg ggccaaggc accactctca cagtctcctc agccaaaaca     420
acacccccat cagtctatcc actggcccct gggtgtggag atacaactgg ttcctctgtg     480
actctgggat gcctggtcaa gggctacttc cctgagtcag tgactgtgac ttggaactct     540
ggatccctgt ccagcagtgt gcacaccttc ccagctctcc tgcagtctgg actctacact     600
atgagcagct cagtgactgt cccctccagc                                     630

<210> SEQ ID NO 9
<211> LENGTH: 609
<212> TYPE: DNA
<213> ORGANISM: Artificial Sequence
<220> FEATURE:
<223> OTHER INFORMATION: Synthesized

<400> SEQUENCE: 9
atgagaccgt ctattcagtt cctggggctc ttgttgttct ggcttcacgg tggtcagtgt      60
gacatccaga tgacacagtc tccatcctca ctgtctgcat cgctgggagg caaagtcacc     120
atcacttgca aggcaagcca agacatttac aagtatattg cttggtacca acacaagcct     180
ggaaaaggtc ctaggctgct catacattac acatctacat gcagccagg catcccatca     240 aggttcagtg aagtgggtc tgggagagat tattccttca gcatcagcga cctggagcct     300
gaagatattg caacttatta ttgtctacag tatgataata ttctgtggac gttcggtgga     360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaag                                                             609
```

What is claimed is:

1. An anti-IL-12Rβ1 antibody comprising a light chain variable region comprising an L1 comprising the sequence set forth in SEQ ID NO: 4, an L2 comprising the sequence YTS, an L3 comprising the sequence set forth in SEQ ID NO: 5, and a heavy chain variable region comprising an H1 comprising the sequence set forth in SEQ ID NO: 1, an H2 comprising the sequence set forth in of SEQ ID NO: 2, an H3 comprising the sequence set forth in SEQ ID NO: 3.

2. The antibody of claim 1, wherein the light chain variable region comprises the sequence set forth in SEQ ID NO: 7 and/or the heavy chain variable region comprises the sequence set forth in SEQ ID NO: 6.

3. The antibody of claim 1, wherein the antibody specifically binds to IL-12Rβ1.

4. The antibody of claim 1, wherein the antibody is a monoclonal antibody or an antibody fragment.

5. The isolated antibody of claim 1, wherein binding of the antibody to IL-12Rβ1 blocks or reduces signaling by IL-23R and/or IL-12R.

6. A pharmaceutical composition comprising an antibody of claim 1 and a pharmaceutically acceptable carrier or excipient.

7. The pharmaceutical composition of claim 6, further comprising a dispersing agent, buffer, surfactant, preservative, solubilizing agent, isotonicity agent, or stabilizing agent.

8. The pharmaceutical composition of claim 7, wherein said carrier comprises physiological saline, ion exchanger, alumina, aluminum stearate, lecithin, serum protein, human serum albumin, buffer, phosphate, glycine, sorbic acid, potassium sorbate, partial glyceride mixture of saturated vegetable fatty acids, water, salts or electrolytes, protamine sulfate, disodium hydrogen phosphate, potassium hydrogen phosphate, sodium chloride, zinc salt, colloidal silica, magnesium trisilicate, polyvinyl pyrrolidone, cellulose, polyethylene glycol, sodium carboxymethylcellulose, polyacrylates, wax, polyethylene-polyoxypropylene-block polymer, polyethylene glycol, wool fat, or a combination thereof.

9. A method of blocking IL-12 and IL-23 signaling in a cell of subject in need thereof, the method comprising: administering a pharmaceutically effective dose of the antibody of claim 1 to the subject or administering an effective dose of a pharmaceutical composition comprising the antibody of claim 1 in combination with at least one pharmaceutically acceptable carrier or excipient to the subject.

10. A method of reducing one or more symptoms of an autoimmune or inflammatory disease in a subject in need thereof, the method comprising: administering a pharmaceutically effective dose of the antibody of claim 1 to the subject or administering an effective dose of a pharmaceutical composition comprising the antibody of claim 1 in combination with at least one pharmaceutically acceptable carrier or excipient to the subject.

11. The method of claim 10, wherein the autoimmune or inflammatory disease is selected from the group consisting of Crohn's disease, inflammatory bowel disease, rheumatoid arthritis, and psoriasis.

12. The method of claim 11, wherein the subject has Crohn's disease and is being treated with or will be treated with anti-TNFα therapy.

13. The method of claim 10, wherein the antibody preferentially targets pathogenic T helper cells expressing high levels of IL12Rβ1.

14. method of claim 10, wherein an effective amount of the antibody prevents STAT3 phosphorylation induced by IL-23 stimulation of the IL-23 receptor.

15. The method of claim 10, wherein an effective amount of the antibody prevents STAT4 phosphorylation induced by IL-12 stimulation of the IL-12 receptor.

16. The method of claim 10, wherein the antibody preferentially targets pathogenic T helper cells expressing high levels of IL12Rβ1.

17. The method of claim 10, wherein an effective amount of the antibody prevents STAT3 phosphorylation induced by IL-23 stimulation of the IL-23 receptor.

18. The method of claim 10, wherein an effective amount of the monoclonal antibody prevents STAT4 phosphorylation induced by IL-12 stimulation of the IL-12 receptor.

* * * * *